(12) United States Patent
Kramer, IV et al.

(10) Patent No.: US 10,602,790 B2
(45) Date of Patent: Mar. 31, 2020

(54) SHOULDER SLING AND PILLOW SYSTEM

(71) Applicants: Warren Kramer, IV, San Clemente, CA (US); Warren Kramer, III, San Clemente, CA (US); Trevor Theriot, Newport, CA (US)

(72) Inventors: Warren Kramer, IV, San Clemente, CA (US); Warren Kramer, III, San Clemente, CA (US); Trevor Theriot, Newport, CA (US)

( * ) Notice: Subject to any disclaimer, the term of this patent is extended or adjusted under 35 U.S.C. 154(b) by 0 days.

(21) Appl. No.: 16/103,403

(22) Filed: Aug. 14, 2018

(65) Prior Publication Data
US 2020/0054084 A1 Feb. 20, 2020

(51) Int. Cl.
*A41D 13/05* (2006.01)
*A41D 27/20* (2006.01)

(52) U.S. Cl.
CPC ....... *A41D 27/205* (2013.01); *A41D 13/0512* (2013.01); *A41D 13/0568* (2013.01); *A41D 27/204* (2013.01)

(58) Field of Classification Search
CPC .................................................. A41D 13/0512

USPC ....................................... 2/16, 59, 71; 5/646
See application file for complete search history.

(56) References Cited

U.S. PATENT DOCUMENTS

| | | | | |
|---|---|---|---|---|
| 526,950 | A * | 10/1894 | Sprung | A41D 13/081 2/66 |
| 2,727,241 | A * | 12/1955 | Smith | A41D 13/081 2/66 |
| 5,911,197 | A * | 6/1999 | Schmid | A01K 15/02 119/709 |
| 6,494,339 | B1 * | 12/2002 | Engelhard | A47G 23/0225 220/475 |
| 6,918,148 | B2 * | 7/2005 | Auxila | A47D 13/083 2/16 |
| 6,931,666 | B1 * | 8/2005 | Brady | A41D 13/08 2/16 |
| 2010/0263100 | A1 * | 10/2010 | Clement | A41D 13/081 2/16 |

* cited by examiner

*Primary Examiner* — Gloria M Hale
(74) *Attorney, Agent, or Firm* — Ruben Alcoba, Esq.

(57) ABSTRACT

A shoulder sling and pillow system that will house a beverage and a cellphone. The system is designed to ergonomically fit around the waist of a user and the system will also allow a cellphone to be charged. The system will use removable straps that will attach to the foam pillow and to the brace of the shoulder sling and pillow system.

5 Claims, 4 Drawing Sheets

SHOULDER SLING AND PILLOW SYSTEM

BACKGROUND

The present invention is directed to a shoulder sling and pillow system that will allow a user to carry at least one item.

The shoulder sling and pillow system of the present invention was developed to allow a user suffering from a shoulder or arm related injury to carry items hands free.

Often, users of shoulder slings injure themselves by attempting to do too much with their uninjured arms.

In order to prevent needless injuries, the inventors of the present invention conceived a pillow that is worn around the waist of a user, below the injured limb or shoulder of the user, that will allow a user to carry a beverage, to house a communication device and that will allow the communication device to be recharged.

The invention is designed to prevent injuries and to improve the quality of life of the user using the present invention.

For the foregoing reason there is a need for a shoulder sling and pillow system that will allow a user to rest an injured arm or limb, that will allow the user to carry items, such as a beverage or cellphone device, hands free, and that will allow the user to charge the communication device.

SUMMARY

The present invention describes a shoulder sling and pillow system that will allow a user to rest an injured arm or limb, that will allow the user to carry items, such as a beverage or cellphone device, hands free, and that will allow the user to charge the communication device.

The shoulder sling and pillow system comprises of a foam pillow that has a cup and cellphone holder integrated within the foam pillow. The foam pillow defines hook and loop attachment means that allow removable straps to be attached to the foam pillow so that the system can be secured around the body of a user. The system also comprises of a brace that uses at least one brace support that allows a user to attach a brace support strap around the neck of a user and thereby help the user support the weight of a limb being secured within the brace. The foam pillow also defines a pocket wherein a power source or any other item can be stored. The power source has a connector that will allow an electronic device to be charged and ideally the connector will have an outlet that will be defined within the cellphone receptacle.

An object of the present invention is to provide a shoulder sling and pillow system that will allow a user to carry a beverage and cellphone hands free.

Another object of the present invention is to provide a shoulder sling and pillow system that will prevent the aggravation of injuries.

DRAWINGS

These and Other Features, Aspects, and Advantages of the Present Invention Will Become Better Understood with Regards to the Following Description, Appended Claims, and Drawings where:

Figure 1:
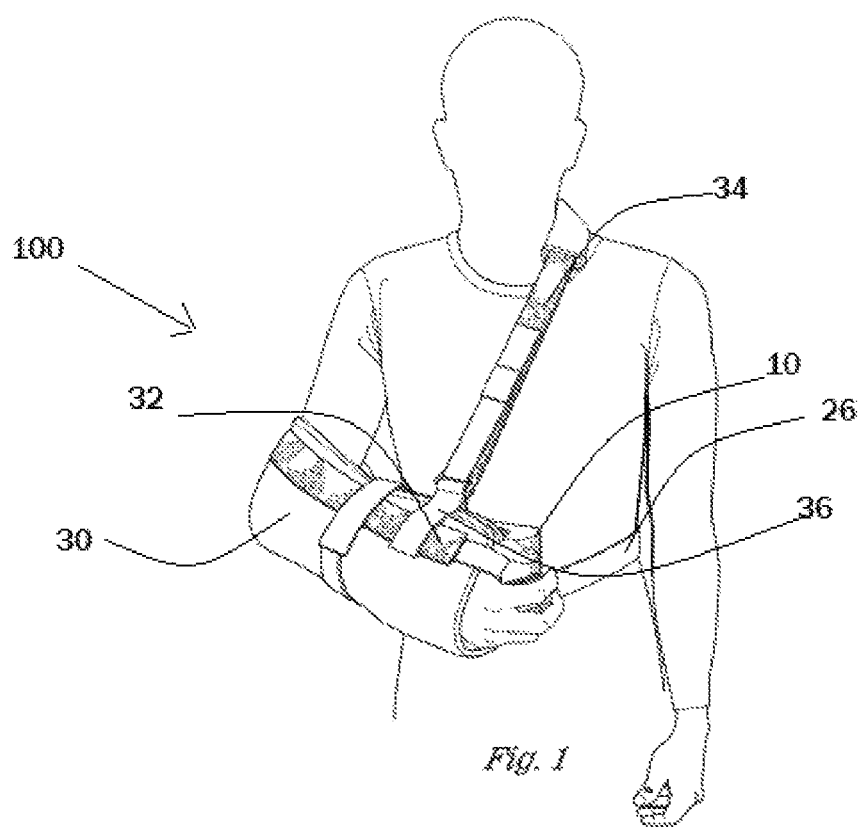
FIG. 1 is a perspective view of showing how the present invention is worn by a user.
Figure 2:
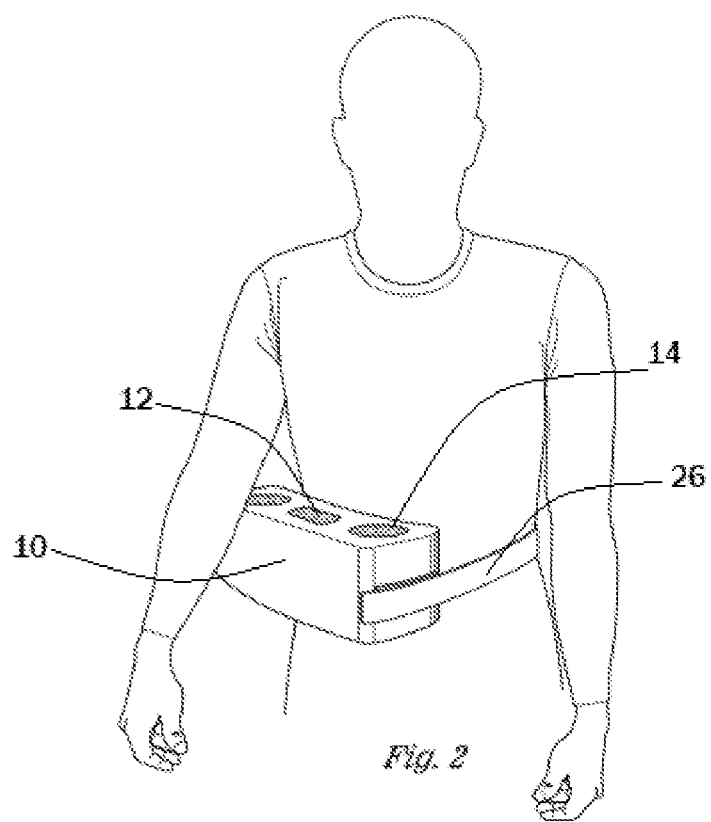
FIG. 2 is a perspective view showing how the foam pillow of the present invention is secured around the waist of a user.
Figure 3:
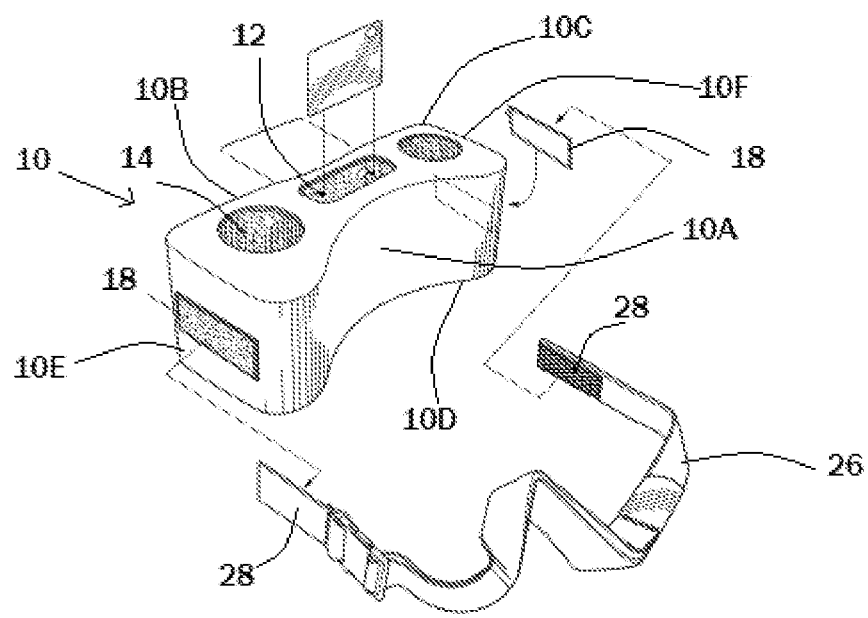
FIG. 3 is perspective view of the foam pillow and the first strap of the present invention.
Figure 4:
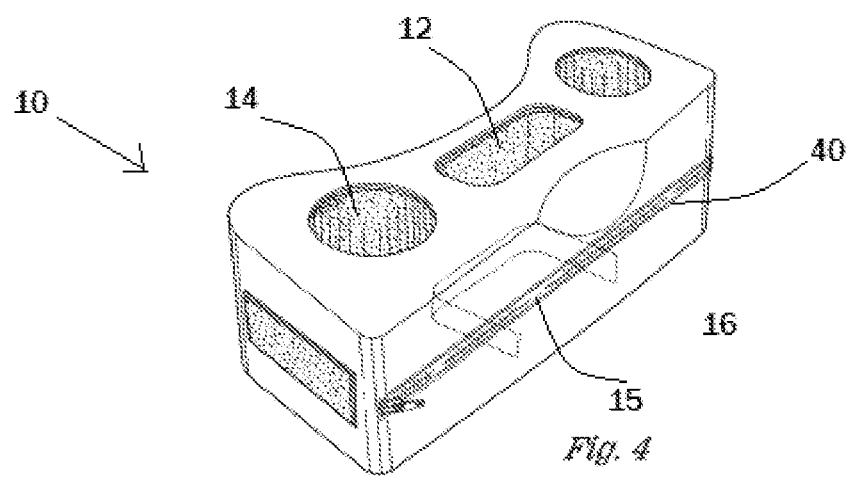
FIG. 4 is a perspective view of the foam pillow of the present invention.
Figure 5:
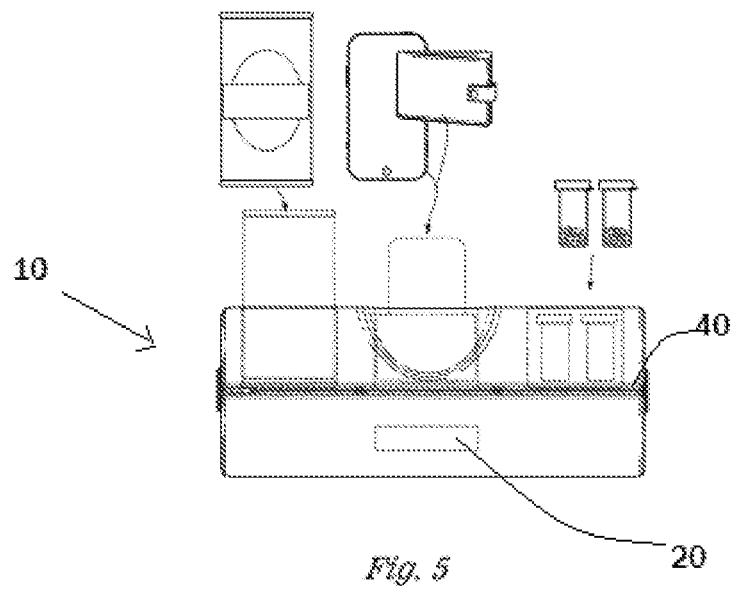
Figure 6:
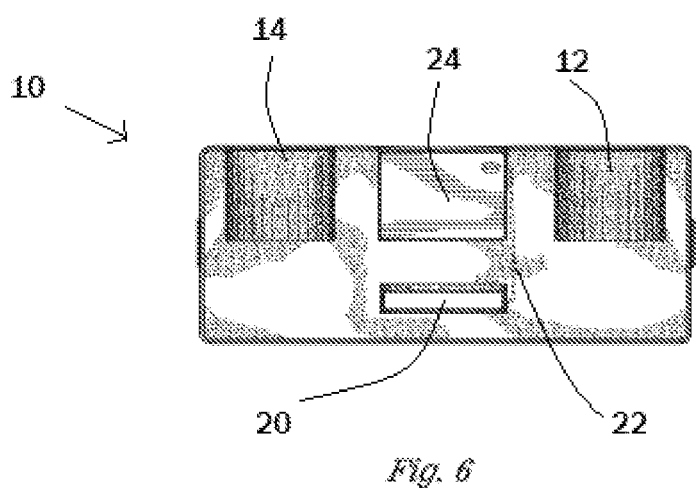

FIG. 5. is a side view of the present invention that shows how a beverage and a cellphone would be inserted within the foam pillow of the present invention; and FIG. 6 is a side view of the present invention that shows a cellphone inserted within the foam pillow of the invention.

DESCRIPTION

As seen in FIGS. 1-6, the present invention describes a shoulder sling and pillow system 100. The shoulder sling and pillow system 100 comprises of a foam pillow 10 having an inner 10*a*, outer 10*b*, upper 10*c*, lower 10*d*, front 10*e* and rear 10*f* part, the inner part 10*a* being contoured to receive the body of the user, the upper part 10*c* defines a cellphone receptacle 12 and at least on receptacle 14 that is designed to hold a cup, the outer part 10*b* defines an opening 15 that leads to a pocket 16, the front 10*e* and rear 10*f* part define a hook and loop material 18. A power source 20 that is housed in the pocket 16, the power source 20 having a connection 22 to the cellphone receptacle 12 that allows a cellphone 24 to be charged. A first strap 26 that has two ends, the ends of the strap define a hook and loop material 28, the first strap 26 attaches to the hook and loom material 18 of the foam pillow 10. A brace 30 that defines at least one brace support 32. And, a shoulder strap 34 that attaches to the brace support 32.

The brace support 32, in an embodiment of the present invention, is a hook and loop attachment and the shoulder strap 34 has a shoulder hook and loop attachments 36 that attaches to the support's hook and loop attachment 32.

The foam pillow 10 is made of a breathable material. The breathable material can be a nylon material.

The opening 15 of the foam pillow can be closed using a zipper 40. The zipper 40 is attached to the foam pillow 10 at a location that allows the opening 15 of the foam pillow 10 to be secured.

An advantage of the present invention is that it provides a shoulder sling and pillow system that allows a user to carry a beverage and cellphone hands free.

Another advantage of the present invention is that it provides a shoulder sling and pillow system that prevents the aggravation of injuries.

While the inventor's above description contains many specificities, these should not be construed as limitations on the scope, but rather as an exemplification of several preferred embodiments thereof. Accordingly, the scope should not be determined by the embodiments illustrated, but by the appended claims and their legal equivalents.

What is claimed is:

1. A shoulder sling and pillow system that is configured for wear by a user, comprising:
    a foam pillow having an inner, outer, upper, lower, front and rear part, the inner part being contoured to receive a body of the user, the upper part defines a cellphone receptacle and at least one receptacle that is designed to hold a cup, the outer part defines an opening that leads to a pocket, the front and rear part define a hook and loop material;
    a first strap that has two ends, the ends of the first strap define a hook and loop material, the strap attaches to the hook and loop material of the foam pillow;
    a brace that defines at least one brace support; and
    a shoulder strap that attaches to the brace support.

2. The shoulder sling and pillow system that is configured for wear by a user of claim 1, comprising a power source that is housed in the pocket, the power source having a connection to the cellphone receptacle that allows a cellphone to be charged.

3. The shoulder sling and pillow system that is configured for wear by a user of claim 2, wherein the brace support is a hook and loop attachment and the shoulder strap hook defines a shoulder hook and loop attachment that attaches to the support's hook and loop attachment.

4. The shoulder sling and pillow system that is configured for wear by a user of claim 3, wherein the foam pillow is covered by a nylon material.

5. The shoulder sling and pillow system that is configured for wear by a user of claim 4, comprising of a zipper that is attached to the foam pillow at a location that will allow the opening of the foam pillow to be secured.

* * * * *